US00PP31600P2

(12) United States Plant Patent
Hansen

(10) Patent No.: US PP31,600 P2
(45) Date of Patent: Mar. 24, 2020

(54) **X *MANGAVE* PLANT NAMED 'FEMME FATALE'**

(50) Latin Name: ***Manfreda* x *Agave* hybrid**
Varietal Denomination: Femme Fatale

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/501,797

(22) Filed: Jun. 7, 2019

(51) Int. Cl.
*A01H 5/00* (2018.01)
*A01H 6/12* (2018.01)

(52) U.S. Cl.
USPC ..... Plt./373
CPC ..... *A01H 6/12* (2018.05)

(58) Field of Classification Search
USPC ..... Plt./373
CPC ..... A01H 5/00
See application file for complete search history.

*Primary Examiner* — Kent L Bell

(57) ABSTRACT

A new and unique x *Mangave* plant named 'Femme Fatale' characterized by compact habit and lanceolate foliage with medium green color and with high ultra violet light exposure developing mottling and blushing to develop nearly solid greyed-purple coloration. Foliage has small semi-flexible marginal teeth and semi-flexible terminal spine. The new plant has a moderate growth rate.

1 Drawing Sheet

Botanical classification: *Manfreda* x *Agave* hybrid.
Variety denomination: 'Femme Fatale'.

STATEMENT REGARDING PRIOR DISCLOSURES UNDER 37 CFR 1.77(B)(6)

The first non-enabling disclosure of the claimed plant, in the form of a private sale, was made by Walters Gardens, Inc. on Jul. 23, 2018 to Plant Delights Nursery, Inc. Plants for this sale were obtained from the inventor. Since then, on Feb. 14, 2019, the plant was first advertised on a website managed by Walters Gardens, Inc. No plants of x *Mangave* 'Femme Fatale' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to the new and distinct x *Mangave* plant, x *Mangave* 'Femme Fatale' hybridized on Jul. 8, 2014 by the inventor at a wholesale perennial nursery in Zeeland, Mich., USA as a cross between x *Mangave* 'Bloodspot' (not patented) as the female or seed parent and an unreleased proprietary hybrid known by the breeder code H10-3 11-SRF-307 (not patented) as the male or pollen parent. Through trials at the same nursery the plant was referred to by the code 14-93-10. The new plant has been successfully asexually propagated initially by removal of basal offsets in 2017 followed by shoot tip tissue culture at the same nursery in Zeeland, Mich. This asexual propagation system has been found to produce stable and identical plants that maintain all the unique characteristics of the original plant in successive generations.

BRIEF SUMMARY OF THE INVENTION

X *Mangave* 'Femme Fatale' differs from its parents as well as all other *Manfreda, Agave* and x *Mangave* known to the applicant. The most similar known x *Mangave* cultivar known to the inventor are: 'Freckles and Speckles' U.S. Plant Pat. No. 30,904, 'Pineapple Express' U.S. Plant Pat. No. 28,613, 'Desert Dragon' U.S. Plant Pat. No. 31,311, 'My Dog Spot' U.S. Plant patent application Ser. No. 16/350,921 and 'Bloodspot' and 'Sponge Paint' copending U.S. Plant patent application Ser. No. 16/602,655.

'Freckles and Speckles' has more glaucous, purplish-gray leaves that are more longitudinally folded. 'Pineapple Express' is more upright in habit and has more numerous upright-pointed leaves with less-overlapping purplish-gray spots. 'Desert Dragon' has more arching foliage with larger spots and smaller, finer and more closely arranged marginal teeth. 'My Dog Spot' has foliage that is more narrow and fleshy with less concentrated and smaller purple-gray spots. 'Bloodspot' is more compact in habit, the leaves are shorter, thicker and more fibrous than the new plant. The male parent, H10-3 11-SRF-307 has flatter habit, narrower foliage that is less fibrous and more succulent with more undulating margins and lack marginal teeth. Both the fraternal grandparents also have flatter habit with fewer leaves per rosette and foliage lacking marginal teeth. One of the fraternal grandparents, a select proprietary non-patented form of *Manfreda maculosa* has more subdued reddish purple coloration. 'Chocolate Chips' (not patented), the other fraternal grandparent, has more intense cupping and undulation of the leaf margins and more intense purple spotting in high ultraviolet light.

The new plant, 'Femme Fatale', is unique from all of these variegated *Agave*, x *Mangave* and *Manfreda* known to the inventor by the following combined traits:

1. Compact habit with over 60 leaves;
2. Foliage lanceolate with small semi-flexible marginal teeth;
3. Foliage develops burgundy speckling to nearly solid greyed-purple with intense ultraviolet light purple blush over the top surface;
4. Moderate growth rate;

BRIEF DESCRIPTION OF THE DRAWINGS

The photograph of the new plant demonstrates the overall appearance of the new plant including the unique traits as a three-year-old plant with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
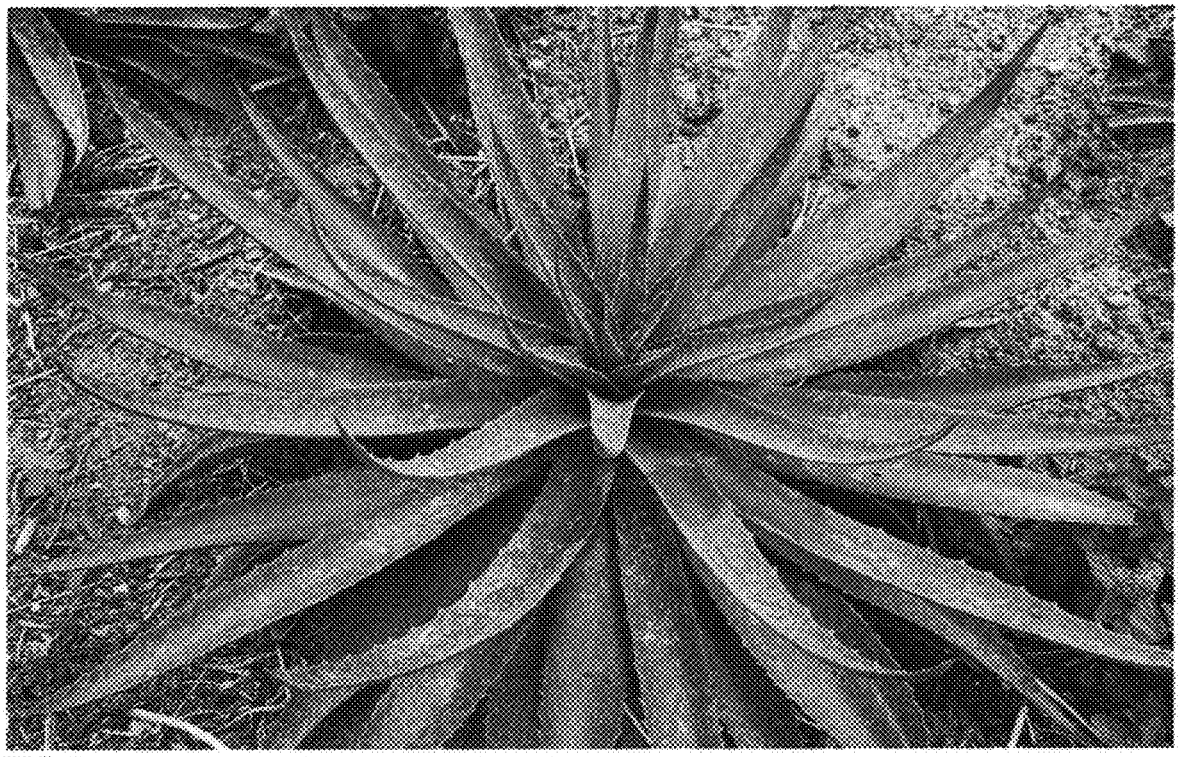
FIG. 1 shows the new plant grown in a full sun trial garden.
Figure 2:
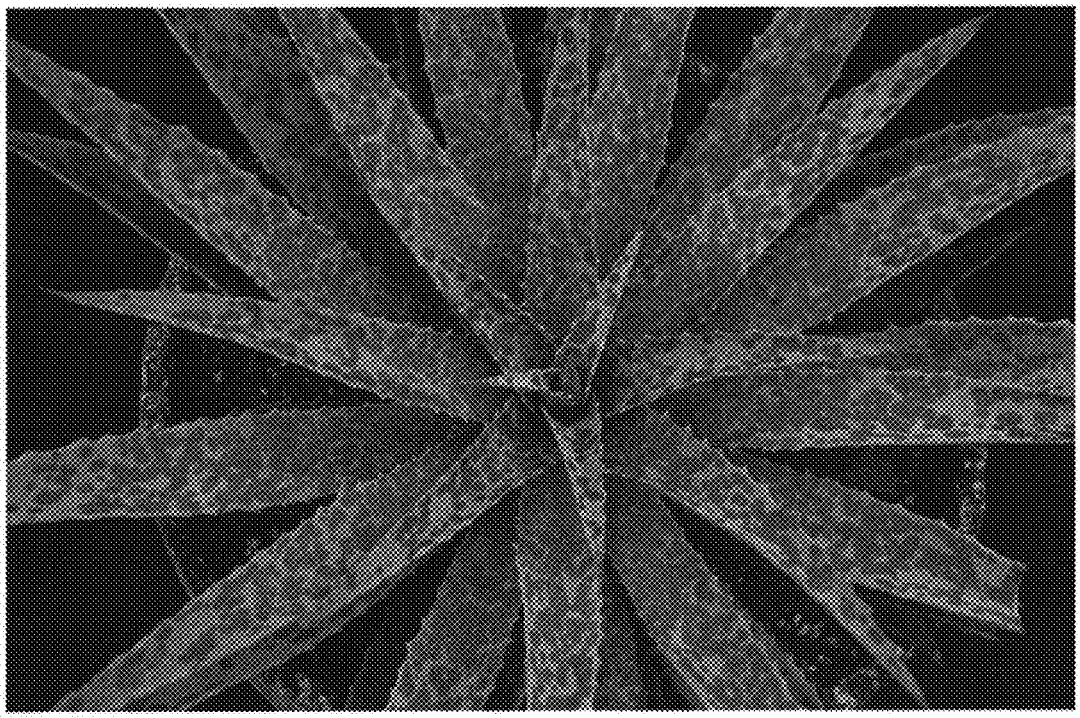
FIG. 2 shows a close-up of the foliage from above grown in a container in a greenhouse.

The following descriptions and color references are based on the 2015 edition of The Royal Horticultural Society Colour Chart except where common dictionary terms are used. The new plant, x *Mangave* 'Femme Fatale', has not been observed under all possible environments. The phenotype may vary slightly with different environmental conditions, such as temperature, light, fertility, moisture and maturity levels, but without any change in the genotype. The following observations and size descriptions are of a three-year old plant in a commercial wholesale greenhouse in Zeeland, Mich. with supplemental water and fertilizer as needed.

Botanical classification: x *Mangave* hybrid (*Manfreda* x *Agave*);

Parentage: 'Bloodspot' as the female or seed parent and H10-3 11-SRF-307 as the male or pollen parent;

Propagation: Division and sterile plant tissue culture;

Time to initiate roots from tissue culture: About 21 days;

Growth rate: Moderate to rapid;

Crop time: About 12 to 16 weeks to finish during lengthening spring days from an established 25 mm tissue culture plug to a 65 mm diameter container;

Rooting habit: Fleshy, lightly branching, with roots up to 15 cm long;

Root color: Nearest RHS 158C;

Plant shape and habit: Succulent herbaceous perennial with basal rosettes of up to about 62 fleshy, radially-emerging and outwardly-facing leaves emerging from a central rhizome, producing a symmetrical flattened mound;

Plant size: Foliage height to about 23.0 cm tall from soil line to the top of the leaves and to about 56.0 cm wide at the widest point at soil line;

Foliage description: Lanceolate; sessile; simple; fleshy, with minimal fibrous content; glabrous; margins finely dentate with semi-flexible teeth; apex acute with semi-flexible mucro; base truncate, sessile, clasping; usually bi-laterally symmetrical;

Leaf size: To about 29.0 cm long, about 4.5 cm wide at base and 4.0 mm thick, average about 28.0 cm long, 3.8 cm wide and 4.0 mm thick; spots of variable sizes from about 0.5 mm diameter to about 8.0 mm long in lower ultraviolet light to nearly complete coverage in high ultraviolet light;

Marginal teeth: Beginning soft and becoming semi-flexible; 1.0 mm to 2.0 mm long and 2.0 mm across at base; average about 10 mm apart;

Mucro or terminal spine: Sharply pointed; glabrous; semi-flexible; straight, about 5.0 mm long;

Foliage fragrance: None observed;

Leaf blade color:

*Adaxial* (*young*).—Young emerging adaxial nearest RHS 137B with spots of nearest RHS 187A.

*Abaxial* (*young*).—Nearest RHS 146C with spots nearest RHS 137B.

*Adaxial* (*mature*).—Nearly solid greyed-purple of nearest blend of RHS 183B and RHS N187D with higher ultraviolet exposure and irregular portions of RHS 147C that are more pronounced distally; with lower ultraviolet exposure predominately RHS 147C with small typically non-overlapping spots of between RHS 183C and RHS N187C.

*Abaxial* (*mature*).—With higher ultraviolet exposure base nearly solid blend of RHS 183B and RHS N187D distally mottle with irregular spaces nearest RHS 138A; with lower ultraviolet exposure blend between RHS 138A and RHS 146B with few spots of nearest RHS 183C.

*Teeth*.—Abaxial and adaxial nearest RHS 181B with tips nearest RHS 159C.

*Mucro*.—On young foliage in strong ultraviolet light nearest RHS 164C in distal 1.0 mm and basal 3.0 to 4.0 mm between RHS 180B and RHS 179B; on mature foliage nearest RHS 176B.

Petiole: Sessile;

Veins: Parallel; not distinct;

Flowering and fruit: Not yet observed;

Disease resistance: X *Mangave* 'Femme Fatale' has not been observed to be resistant to diseases common to other x *Mangave* beyond that which is normal for *Agave* or *Manfreda*. The plant is xeromorphic and survives well with minimal water once established. Hardiness at least from USDA zone 9 to 11. Full extent of winter hardiness has not been tested.

I claim:

1. A new and distinct cultivar of ornamental x *Mangave* plant named 'Femme Fatale' as herein described and illustrated.

* * * * *